(12) United States Patent  
Zeller et al.

(10) Patent No.: US 7,521,579 B2  
(45) Date of Patent: Apr. 21, 2009

(54) PROCESS FOR THE PREPARATION OF ALPHA HYDROXYCARBOXYLIC ACID AMIDES

(75) Inventors: Martin Zeller, Muenchwilen (CH); Dominik Faber, Muenchwilen (CH); Thomas Vettiger, Basel (CH); Clemens Lamberth, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 675 days.

(21) Appl. No.: 10/495,257

(22) PCT Filed: Nov. 15, 2002

(86) PCT No.: PCT/EP02/12844

§ 371 (c)(1),  
(2), (4) Date: May 7, 2004

(87) PCT Pub. No.: WO03/042166

PCT Pub. Date: May 22, 2003

(65) Prior Publication Data

US 2005/0014950 A1    Jan. 20, 2005

(30) Foreign Application Priority Data

Nov. 16, 2001    (GB) .................. 0127559.3

(51) Int. Cl.  
*C07C 233/05* (2006.01)  
*C07C 231/02* (2006.01)

(52) U.S. Cl. ................. 564/170; 564/134; 564/139; 564/140

(58) Field of Classification Search ......... 564/170, 564/134, 139, 140  
See application file for complete search history.

(56) References Cited

U.S. PATENT DOCUMENTS 5,292,521 A * 3/1994 Shino et al. ............ 424/484

FOREIGN PATENT DOCUMENTS

| GB | 2122617 | 1/1984 |
| JP | 55045604 | 3/1980 |
| SU | 1436454 | 6/1993 |
| WO | 9429267 | 12/1994 |
| WO | 0049118 | 7/2000 |
| WO | 0187822 | 11/2001 |

OTHER PUBLICATIONS

Anoury et al, J.C.S. Perkin Trans. I, (9), 1015-17, 1974.*  
Organic preparations and Procedures International, 15(1-2), 49-55, 1983.(Only reaction abstract provided).*  
Gordon et al, Organic Preparations and Procedures, Int, 15(1-2), 49-55, 1983.*

Reiner Luckenbach: "Beilsteins Handbuch der Organischen Chemie, 4th Edition, Suppl. 4, vol. 13"; 1985 Springer-Verlag, Berlin Heidelberg New York Tokyo XP002231833, p. 2603.  
Database Corssfire Beilstein 'Online! Bweilstein Institut Zur Foerderung Der Chemischen Wissenschaften, Frankfurt Am Main, DE; Database-Accession No. 2805360 (BRN), XP002231834 & J. Arch. Pharm Ber. Dtsch. Pharm Ges., vol. 297, 1964, pp. 282-291.  
E. McDonald et al.: "Synthesis of unsymmertrical dibensylketones: . . . ", Tetrahedron Letters., vol. 15, 1977, pp. 1317-1320.

(Continued)

*Primary Examiner*—Shailendra Kumar  
(74) *Attorney, Agent, or Firm*—Thomas Hamilton

(57) ABSTRACT

The invention concerns a novel process for the preparation of 2-phenyl-2-hydroxy-N-[2-(3-alkoxy-4-hydroxyphenyl)-ethyl]-acetamides of the formula (I), wherein $R_1$ is alkyl, $R_2$ and $R_3$ are each independently hydrogen or alkyl, and $R_4$ is optionally substituted aryl or optionally substituted heteroaryl, which process comprises reacting a 2-(3-alkoxy-4-hydroxyphenyl)-ethylamine of the formula (II), wherein $R_1$ $R_2$ and $R_3$ are as defined above with a α-hydoxycarboxylic acid ester of the formula (III) or a dioxolanone of the formula (III)a, wherein $R_4$ is as defined above, and $R_5$, $R_6$ and $R_7$ independently of each other are lower alkyl. The compounds of formula (I) are important intermediates for a novel group of fungicides derived from mandelic acid amides.

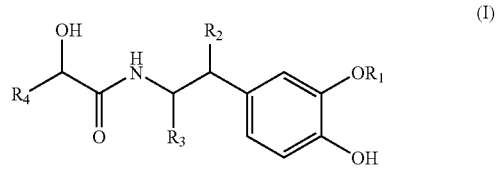

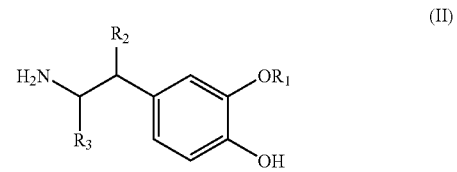

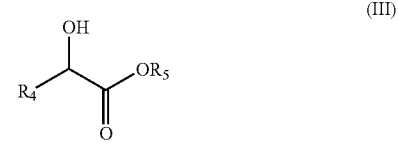

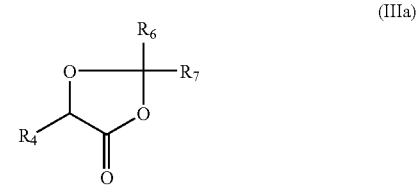

15 Claims, No Drawings

OTHER PUBLICATIONS

Schafer, H. et al: "Enantioselective Conjugate Addition of Primary Dialkylzinc Reagents to 2-Aryl- and 2-Heteroaryl-nitroolefins Mediated by Titanium-Taddolates Preparation of Enantionenriched 2-Aryl-alkylamines"; vol. 51, No. 8, Feb. 20, 1995; pp. 2305-2324.

Patent Abstracts of Japan, vol. 004, No. 081 (c-014), Jun. 11, 1980 & JP 55 045604 A (Sagami Chem Res Center), Mar. 31, 1980; cited in application abstract.

Chemical Abstracts, vol. 72, No. 11, Mar. 16, 1970; Columbus, Ohio, US; Abstract No. 54927n, Sheth et al.: "Synthesis of homovanillinamine by Clemmensen reduction" & Indian J. Appl. Chem., vol. 31, No. 3-4, 1968, pp. 137-138.

Database WPI Section Ch, Week 1999441, Derwent Publications Ltd., AN 1994-330806, & SU 1 436 454 A (Medicinal Plants Res Inst), Jun. 23, 1993; abstract.

Reiner Luckenbach: "Beilsteins Handbuch der Organischen Chemie, vol. XIII, 4$^{th}$ Edition, 4$^{th}$ Suppl., p. 2603", 1985, Springer-Verlag, Berlin Heidelberd, p. 2603.

Peter Tinapp: Herstellung von Mandelaldehyden . . . Chemische Berichte., vol. 104. No. 7, 1971, pp. 2266-2272, Weinheim DE , p. 2266 to 2268; p. 2270, last paragraph; table 3.

Johannes S. Buck: "Catalytic reduction of mandelonitriles"; Journal of the American Chemical Society; vol. 55, 1933, pp. 2593-2597.

* cited by examiner

PROCESS FOR THE PREPARATION OF ALPHA HYDROXYCARBOXYLIC ACID AMIDES

This application is a 371 of International Application No. PCT/EP02/12844 filed Nov. 15, 2002, which claims priority to GB 0127559.3, filed Nov. 16, 2001, the contents of which are incorporated herein by reference.

The present invention relates to a process for the production of α-hydroxycarboxylic acid amides which are valuable intermediates for the production of fungicidally active compounds. The present invention further relates to novel intermediates used in the process according to the invention.

The α-hydroxycarboxylic acid amides which can be produced by the process according to the present invention may be used as intermediates for fungicidally active phenyl-propargylether derivatives which are described, for example, in WO 01/87822. These fungicidally active phenyl-propargylether derivatives correspond to the formula Ia

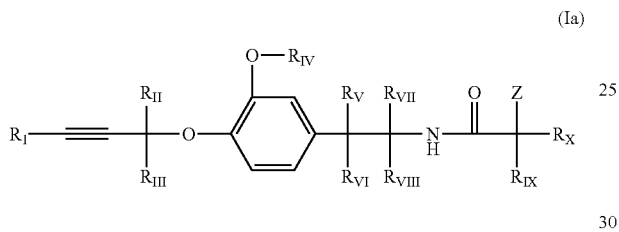

(Ia)

wherein $R_I$ is hydrogen, alkyl, cycloalkyl or optionally substituted aryl, $R_{II}$ and $R_{III}$ are each independently hydrogen or alkyl, $R_{IV}$ is alkyl, $R_V$, $R_{VI}$, $R_{VII}$, and $R_{VIII}$ are each independently hydrogen or alkyl, $R_{IX}$ is hydrogen, optionally substituted alkyl, optionally substituted alkenyl or optionally substituted alkynyl, $_X$ is optionally substituted aryl or optionally substituted heteroaryl, and Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl, including the optical isomers thereof and mixtures of such isomers.

In WO 01/87822 a variety of methods for the preparation of the compounds of the above formula Ia have been described with reference to reaction schemes 1 to 4 a which are briefly discussed below.

Scheme 1:

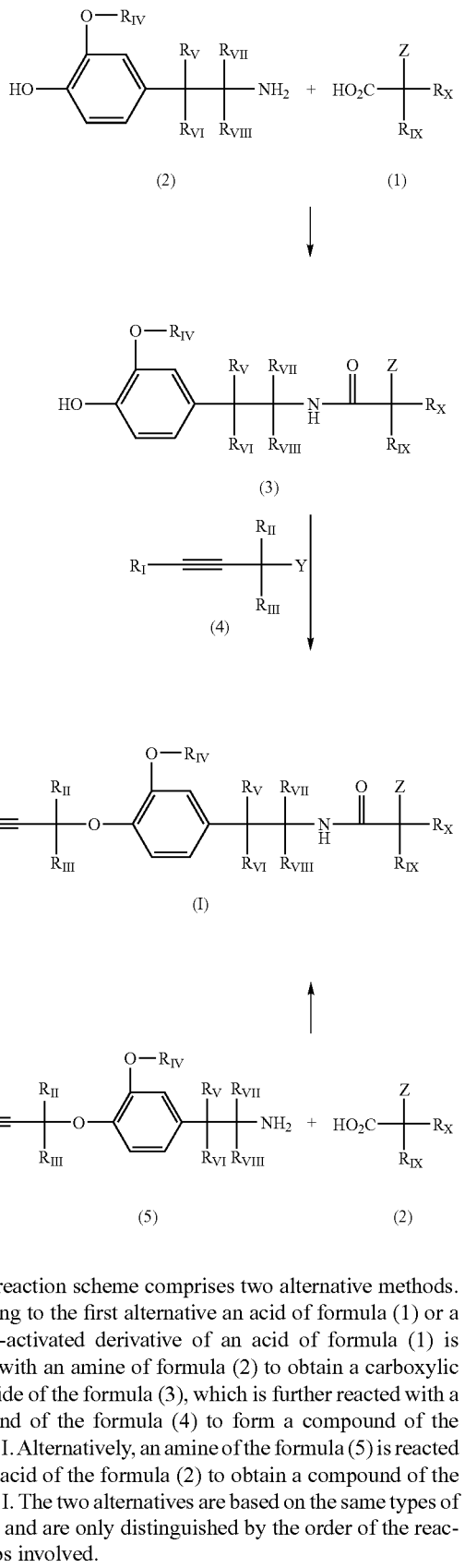

This reaction scheme comprises two alternative methods. According to the first alternative an acid of formula (1) or a carboxy-activated derivative of an acid of formula (1) is reacted with an amine of formula (2) to obtain a carboxylic acid amide of the formula (3), which is further reacted with a compound of the formula (4) to form a compound of the formula I. Alternatively, an amine of the formula (5) is reacted with an acid of the formula (2) to obtain a compound of the formula I. The two alternatives are based on the same types of reaction and are only distinguished by the order of the reaction steps involved.

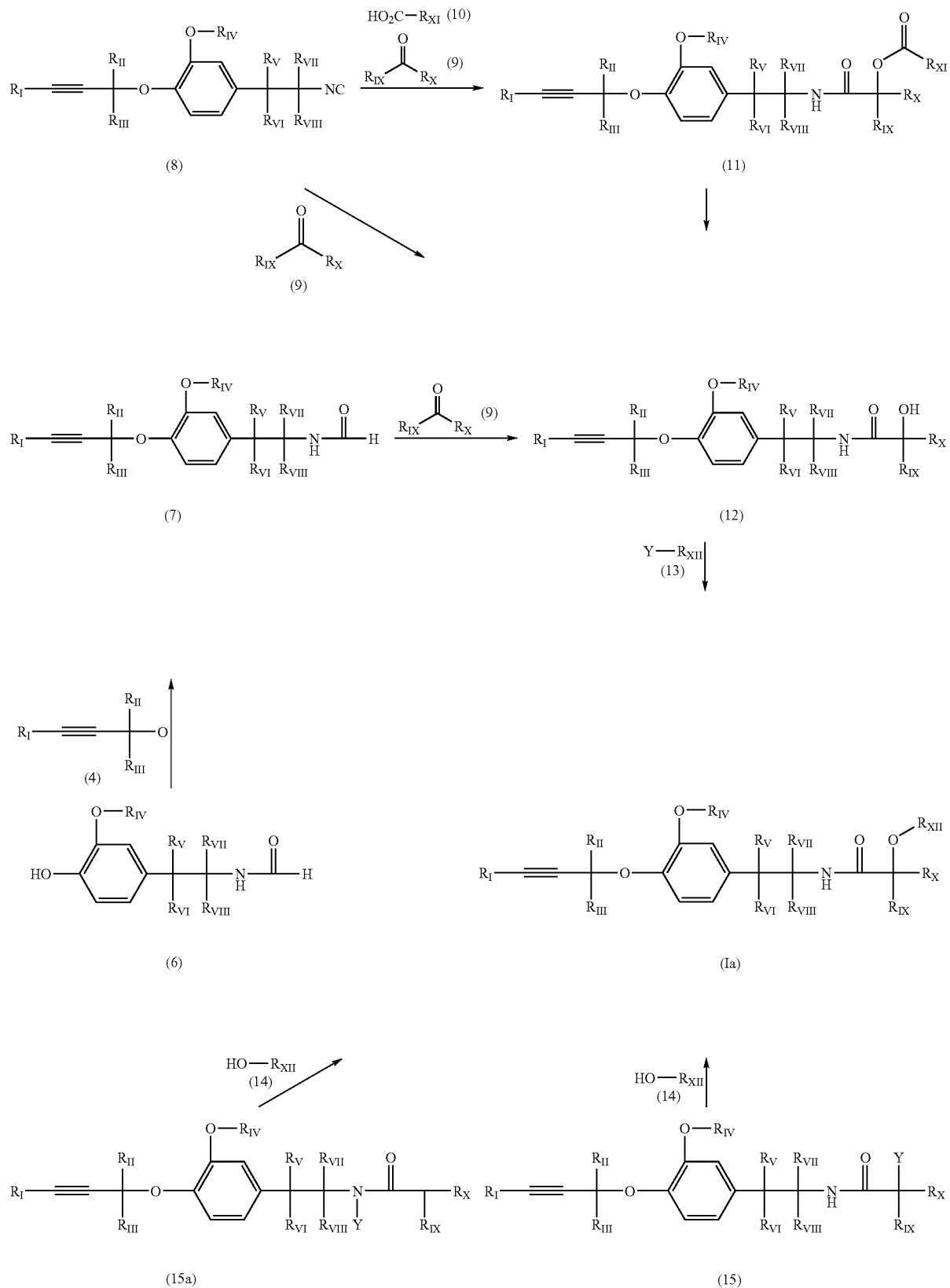
Scheme 2: Preparation of compounds of subformula Ia

According to this scheme compounds of subformula Ia are prepared starting from N-formyl-2-(4-hydroxyphenyl)-ethylamine (6) which is etherified with compound (4) to compound (7) the N-formyl group of which is converted into a isonitrile group as shown in compound (8). Isonitrile (8) is reacted with ketone (9) in the presence of acid (10) to α-hydroxy acid ester (11) which is hydrolysed to α-hydroxyacid amide (12), which compound can also be obtained directly from isonitrile (8) or from N-formyl compound (7) by reaction with ketone (9). The α-hydroxyacid amide (12) is then reacted with compound (13) to form the compound of the subformula Ia which compound can alternatively be obtained by reacting either compound (15) or compound (15a) with hydroxy-compound (14).

-continued

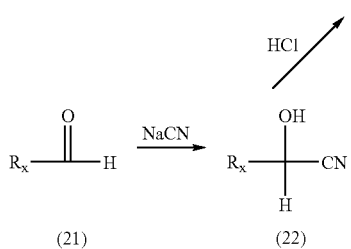

Scheme 3: Preparation of intermediates of formula (12):

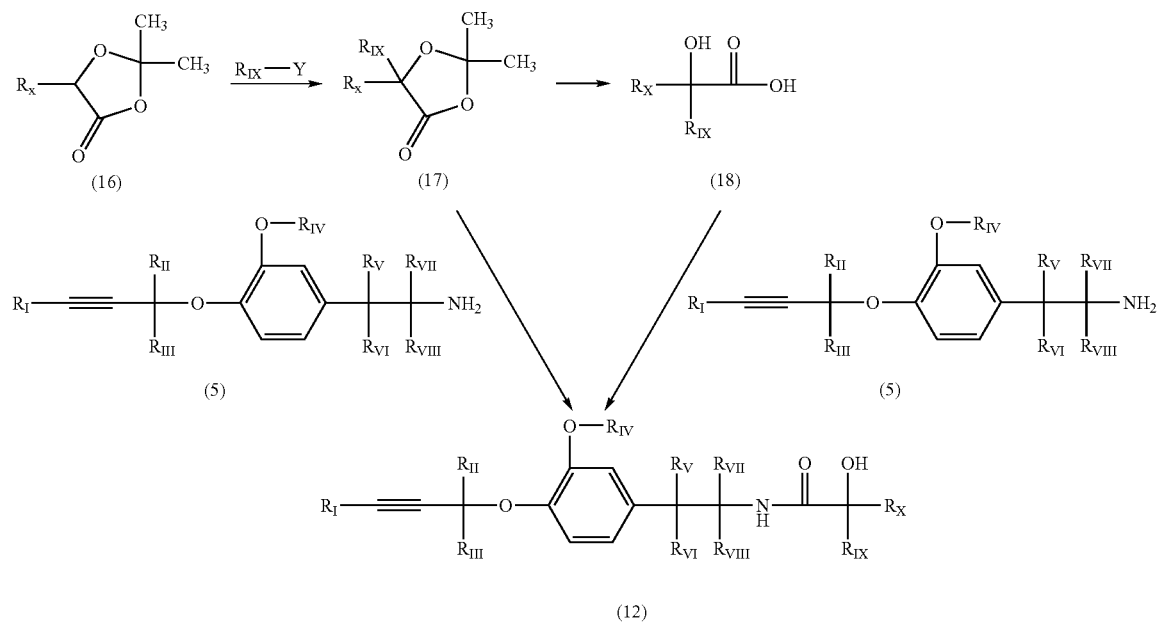

According to this method a dioxolanone (16) which can be obtained by reacting the corresponding α-hydroxyacid with acetone in the presence of a strong acid is alkylated to form a dioxolanone (17) or the corresponding α-hydroxyacid (18) is then reacted with substituted 2-phenylethylamine (5) to obtain a compound (12).

Scheme 4: Preparation of compounds of subformula Ib

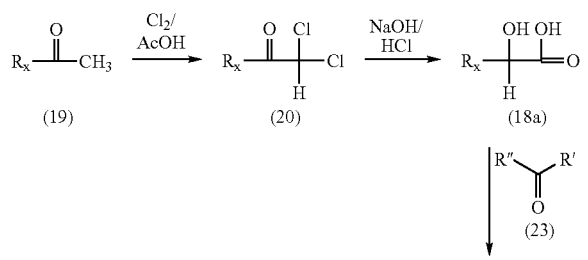

-continued

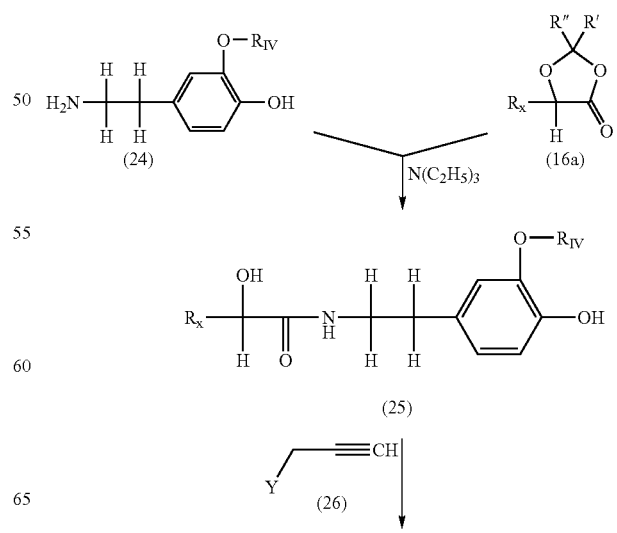

-continued

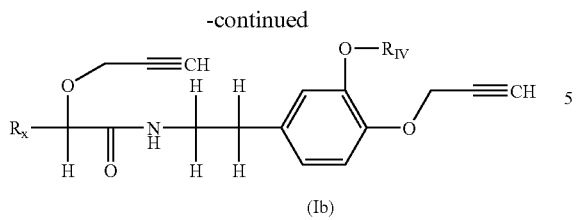

(Ib)

According to this method a α-hydroxyacid (18a), which can be obtained either by chlorinating a ketone (19) in acetic acid and hydrolyzing the α, α-dichloroketone (20) or by transforming an aldehyde (21) into the corresponding cyanohydrin (22) and hydrolyzing of the latter, is reacted with a ketone (23) to form a dioxolanone (16a). The dioxolanone (16a) thus obtained is then reacted with a 2-(4-hydroxyphenyl)-ethylamine (24) to obtain carboxylic acid amide (25) which is di-etherified with compound (26) to obtain a compound of the subformula Ib.

In view of the excellent fungicidal activity of the phenyl-propargylether derivatives of the above formula Ia there exists a need for a process for their preparation which is suitable to be performed on an industrial scale. Since the processes contemplated in the hitherto unpublished co-pending international application PCT/EP01/05530 are not satisfactory for that purpose it is the object of the present invention to provide a process for the preparation of intermediates which can be easily transformed into the phenyl-propargylether derivatives of the above formula Ia.

According to the present invention it is suggested to prepare 2-phenyl-2-hydroxy-N-[2-(3-alkoxy-4-hydroxyphenyl)-ethyl]-acetamides of the formula I

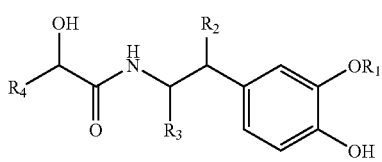

(I)

wherein
$R_1$ is alkyl,
$R_2$, and $R_3$ are each independently hydrogen or alkyl, and
$R_4$, is optionally substituted aryl or optionally substituted heteroaryl, by a process which comprises reacting an 2-(3-alkoxy-4-hydroxyphenyl)-ethylamine of the formula II

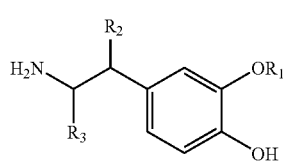

(II)

wherein $R_1$, $R_2$ and $R_3$ are defined above with a α-hydoxycarboxylic acid ester of the formula III or a dioxolanone of the formula IIIa

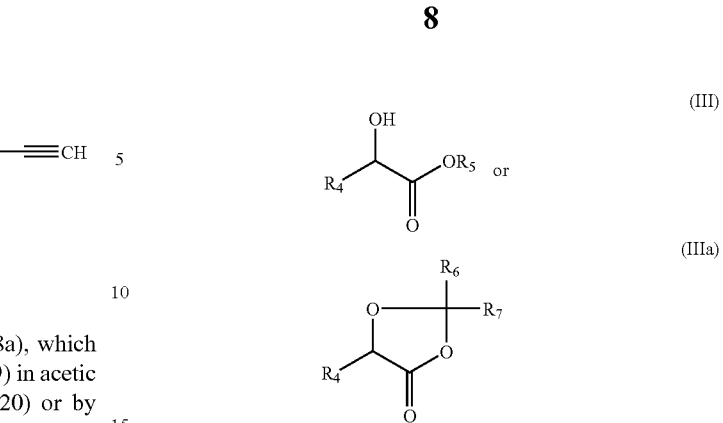

wherein $R_4$ is as defined above, and $R_5$, $R_6$ and $R_7$ independently of each other are lower alkyl.

According to a one embodiment the process is carried out in the absence of a solvent at a temperature at or above the melting temperature of the reaction mixture. The process according to the present invention is advantageously carried out by intimately mixing a 2-(3-alkoxy-4-hydroxyphenyl)-ethylamine of the formula II with a α-hydroxycarboxylic acid ester of the formula III and heating the mixture to a temperature within the range from the melting temperature of the reaction mixture and a temperature of up to +100° C. above the melting temperature of the reaction mixture. Preferably the reaction is carried out at a temperature within the range of from the melting temperature and a temperature of +50° C. above the melting temperature of the reaction mixture, and most preferably at a temperature of from the melting temperature and a temperature of +20° C. above the melting temperature of the reaction mixture.

The α-hydroxycarboxylic acid ester of the formula III or IIIa and the 2-(3-alkoxy-4-hydroxyphenyl)-ethylamine of the formula II may be used in a molar ratio of from 1:2, preferably 1:1,2. Most preferably the α-hydroxycarboxylic acid ester of the formula III and the 2-(3-alkoxy-4-hydroxyphenyl)-ethylamine of the formula II are used in equimolar amount. According to a preferred embodiment the reaction of a 2-(3-alkoxy-4-hydroxyphenyl)-ethylamine of the formula II in the absence of a solvent to a 2-aryl-2-hydroxy-N-[2-(3-alkoxy-4-hydroxyphenyl)-ethyl]-acetamideis carried out with an α-hydroxycarboxylic acid ester of the formula III.

As a rule the reaction can be carried out in the absence of a catalyst. However, if acidic impurities are present, such as traces of the carboxylic acid of the ester used, a base can be advantageously added to the reaction mixture in order to complete the reaction. Suitable bases are, for example, tertiary amines, such as triethylamine.

As a rule the molten product obtained by the process according to the present invention can be immediately used for the further conversion into a compound of the formula Ia. If necessary, the molten product can be dissolved in an organic solvent and purified by crystallization and/or extraction. Further, it is possible, to dissolve the product in an aqueous base, such as sodium hydroxide or potassium hydroxide, and further reacting the corresponding phenolate salt formed in a two-phase system in the presence of a phase transfer catalyst. In comparison to the previously described process in which a solvent is used, the process according to the invention is advantageous in that a considerably shorter reaction time is needed. Further, the yield per volume of the process according to the invention is higher than in the previously described process and the conversion to the desired α-hydroxycarboxylic acid amide of the formula I is practically quantitative.

According to another embodiment the reaction of a 2-(3-alkoxy-4-hydroxyphenyl)-ethyl-amine of the formula II with a α-hydroxycarboxylic acid ester of the formula III or IIIa is carried out in the presence of an inert solvent and in the presence of an organic or inorganic base at a temperature within the range of from −80° C. to +200° C.

Suitable solvents are, for example, aromatic and aliphatic or halogenated optionally halogenated hydrocarbons, ethers, alcohols and nitriles. Especially suitable solvents are chlorohydrocarbons, such as dichloromethane or chlorobenzene, hydrocarbons, such as n-hexane, cyclohexane or toluene, ethers, such as diethylether, tert-butyl-methyl ether, dioxane or tetrahydrofuran, alcohols, such as methanol, ethanol, propanol, isopropanol or sec-butanol. Mixtures of the aforementioned solvents can also be used.

Suitable organic bases are, for example, triethylamine, N,N-diisopropyl-ethylamine, pyridine, N-methylpiperidine and N-methylmorpholine. Examples for suitable inorganic bases are sodium carbonate and potassium carbonate.

Within the temperature range of from −80° C. to +200° C. the range of 0° C. to +140° C. is preferred.

The reaction of a 2-(3-alkoxy-4-hydroxyphenyl)-ethylamine of the formula 11 to a 2-aryl-2-hydroxy-N-[2-(3-alkoxy-4-hydroxyphenyl)-ethyl]-acetamide of the formula I in the presence of an inert solvent is preferably carried out with a dioxolanone compound of the formula IIIa.

The dioxolanones of the formula IIIa are novel compounds and are, therefore, also a part of the present inventive concept.

The dioxolanones of the formula IIIa may be obtained by reacting an α-hydroxyacid of the formula IV

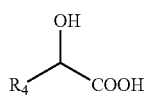

(IV)

wherein $R_4$ is as defined for formula I, in the presence of a strong acid with a ketone of the formula V

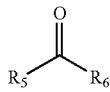

(V)

wherein $R_5$ and $R_6$ are each independently of each other lower alkyl.

Suitable strong acids are hydrochloric acid, sulfuric acid, benzene sulfonic acid, methane sulfonic acid, and nitric acid, with sulfuric acid being preferred. Lower alkyl groups $R_5$ and $R_6$ contain 1 to 4 carbon atoms. Preferably $R_5$ and $R_6$ represent methyl or ethyl and most preferably methyl.

In the above definition of the formula I aryl includes aromatic hydrocarbon rings like phenyl, naphthyl, anthracenyl, phenanthrenyl and biphenyl like 1,3-biphenyl and 1,4-biphenyl, with phenyl being preferred. The same definition applies where aryl is part of aryloxy or arylthio. Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may be optionally substituted. This means that they may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenylalkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl.

Typical examples include 4-chlorophenyl, 4-bromophenyl, 3,4-dichlorophenyl, 4-chloro-3-fluorophenyl, 3-chloro-4-fluorophenyl, 4-methylphenyl, 4-ethylphenyl, 4-propargyloxyphenyl, 1-naphthyl, 2-naphthyl, 4-biphenylyl, 4'-chloro-4-biphenylyl, 5-chloro-thien-2-yl, 5-methyl-thien-2-yl, 5-methyl-fur-2-yl, 5,6,7,8-tetrahydro-1-naphthyl, 5,6,7,8-tetrahydro-2-naphthyl, 3,4-dioxomethylenyl-phenyl, 3,4-dioxoethylenyl-phenyl, 6-benzothienyl, 7-benzothienyl, 3-methylphenyl, 4-fluorophenyl, 4-ethenylphenyl, 4-ethynylphenyl, 4-propylphenyl, 4-isopropylphenyl, 4-tert-butylphenyl, 4-ethoxyphenyl, 4-ethynyloxyphenyl, 4-phenoxyphenyl, 4-methylthiophenyl, 4-methylsulfonylphenyl, 4-cyanophenyl, 4-nitrophenyl, 4-methoxycarbonyl-phenyl, 3-bromophenyl, 3-chlorophenyl, 2-chlorophenyl, 2,4-dichlorophenyl, 3,4,5-trichlorophenyl, 3,4-difluorophenyl, 3,4-dibromophenyl, 3,4-dimethoxyphenyl, 3,4-dimethylphenyl, 3-chloro-4-cyanophenyl, 4-chloro-3-cyanophenyl, 3-bromo-4-methylphenyl, 4-methoxy-3-methylphenyl, 3-fluoro-4-methoxyphenyl, 4-chloro-3-methylphenyl, 4-chloro-3-trifluoromethyl-phenyl, 4-bromo-3-chlorophenyl, 4-trifluoromethylphenyl, 4-trifluoromethoxyphenyl, 4-methoxyphenyl, 4'-methyl-4-biphenylyl, 4'-trifluoromethyl-4-biphenylyl, 4'-bromo-4-biphenylyl, 4'-cyano-4-biphenylyl, 3'4'-dichloro-4-biphenylyl, etc.

Again, the same optional substituent may be present where aryl is part of aryloxy or arylthio. Optionally substituted alkyl groups may carry one or more substituents selected from halogen, alkyl, alkoxy, alkylthio, cycloalkyl, phenyl, nitro, cyano, hydroxy, mercapto, alkylcarbonyl or alkoxycarbonyl. This also applies where alkyl is part of another substituent like alkoxy, alkylthio, alkylsulfinyl, alkylsulfonyl.

Preferably, the number of substituents is no more than three with the exception of halogen, where the alkyl groups may be perhalogenated.

In the above definitions "halogen" includes fluorine, chlorine, bromine and iodine.

The alkyl radicals may be straight-chain or branched. This applies also to the alkyl parts of other alkyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclobutyl, cyclopentyl, cyclohexyl, cycloheptyl or cyclooctyl.

Depending upon the number of carbon atoms mentioned, alkenyl as a group or as a structural element of other groups is to be understood as being, for example
—CH=CH$_2$, —CH$_2$—CH=CH$_2$, —CH=CH—CH$_3$, —CH$_2$—CH=CH—CH$_3$, —CH$_2$—CH$_2$—CH=CH$_2$, —CH$_2$—CH(CH$_3$)—CH=CH$_2$, —CH$_2$—C(CH$_3$)=CH$_2$, —CH=CH—(CH$_2$)$_2$—CH$_3$, —CH$_2$—CH$_2$—CH=CH—CH$_3$, —CH$_2$—CH$_2$—C(CH$_3$)=CH—CH$_3$, —CH(CH$_3$)—CH$_2$—CH=CH—CH$_3$, —CH$_2$—CH$_2$—CH=CH—CH$_3$, —CH=CH—(CH$_2$)$_3$—CH$_3$, —CH$_2$—CH$_2$—CH=C(CH$_3$)—CH$_3$, —CH$_2$—CH$_2$—CH=C(CH$_3$)—CH$_2$-CH$_3$, —C(CH$_3$)=CH$_2$, —CH(CH$_3$)—CH=CH$_2$, —CH(CH$_3$)—CH=CH—CH$_3$, —CH(CH$_3$)—CH$_2$—CH=CH$_2$, —CH$_2$—CH(CH$_3$)—C(CH$_3$)=CH$_2$, —CH$_2$—C(CH$_3$)=CH—CH$_3$, —C(CH$_3$)=CH—(CH$_2$)$_2$—CH$_3$, —CH(CH$_3$)—CH$_2$—C(CH$_3$)=CH—CH$_3$, —CH(CH$_3$)—(CH$_2$)$_2$—CH=CH$_2$, —C(CH$_3$)=CH—(CH$_2$)$_3$—CH$_3$, —CH(CH$_3$)—CH$_2$—CH=CH—CH$_2$—CH$_3$, —(CH$_2$)$_3$—CH=CH$_2$, —C(CH$_3$)=CH—CH$_3$, —CH(CH$_3$)—CH$_2$—C(CH$_3$)=CH—CH$_3$, or —CH(CH$_3$)—CH$_2$—CH=CH—CH$_3$.

Alkynyl as a group or as a structural element of other groups is, for example
—C≡CH, —CH$_2$—C≡CH, —C≡C—CH$_3$, —CH$_2$—C≡C—CH$_3$, —CH$_2$—CH$_2$—C≡CH, —C≡C—CH$_2$—CH$_3$, —CH$_2$—CH(CH$_3$)—C≡CH, —C≡C—(CH$_2$)$_2$—CH$_3$, —CH$_2$—CH$_2$—C≡C—CH$_3$, —CH(CH$_3$)—CH$_2$—C≡C—CH$_3$, —CH$_2$—CH$_2$—C≡C—CH$_2$—CH$_3$, —C≡C—(CH$_2$)$_3$—CH$_3$, —C≡C—(CH$_2$)$_4$—CH$_3$, —CH(CH$_3$)—C≡CH, —CH(CH$_3$)—C≡C—CH$_3$, —CH(C$_2$H$_5$)—C≡C—CH$_3$, —CH(CH$_3$)—CH$_2$—C≡CH, —CH(CH$_3$)—(CH$_2$)$_2$—C≡CH, —CH(CH$_3$)—CH$_2$—C≡C—CH$_2$—CH$_3$, —(CH$_2$)$_3$—C≡CH, or —CH(CH$_3$)—CH$_2$—C≡C—CH$_2$—CH$_3$, depending on the number of carbon atoms present.

A haloalkyl group may contain one or more (identical or different) halogen atoms, and for example may stand for CHCl$_2$, CH$_2$F, CCl$_3$, CH$_2$Cl, CHF$_2$, CF$_3$, CH$_2$CH$_2$Br, C$_2$Cl$_5$, CH$_2$Br, CHClBr, CF$_3$CH$_2$, etc . . .

The presence of at least one asymmetric carbon atom in the compounds of formula I means that the compounds may occur in optically isomeric and enantiomeric forms. As a result of the presence of a possible aliphatic C=C double bond, geometric isomerism may also occur. Formula I is intended to include all those possible isomeric forms and mixtures thereof.

The optical isomers of compounds of the formula I can be prepared, for example, by reacting a 2-phenylethylamine of the formula IV with the optical isomers R- or the S-isomers, i.e. the (+)- or the (−)-form, of an α-hydroxycarboxylic acid in order to form the corresponding R- or S-enantiomer of a compound of the formula IV. The reaction can be advantageously carried out at room temperature in an aprotic solvent, for example dimethylformamide, in the presence of a catalyst, such as a quaternary phosphonium compound, for example, (benzotriazol-1-yloxy)-tris-(dimethylamino)-phosphonium hexafluorophosphate.

For example, (R)-2-hydroxy-2-(4-bromophenyl)-N-[2-(3-methoxy-4-hydroxyphenyl)-ethyl]-acetamide, (S)-2-hydroxy-2-(4-bromophenyl)-N-[2-(3-methoxy-4-hydroxyphenyl)-ethyl]-acetamide, (R)-2-hydroxy-2-(4-chlorophenyl)-N-[2-(3-methoxy-4-hydroxyphenyl)-ethyl]-acetamide and (S)-2-hydroxy-2-(4-chlorophenyl)-N-[2-(3-methoxy-4-hydroxyphenyl)-ethyl]-acetamide can be prepared in this manner.

Preferred subgroups of compounds of formula I are those wherein
$R_1$ is $C_1$-$C_8$alkyl; or
$R_1$ is $C_1$-$C_6$alkyl; or
$R_1$ is $C_1$-$C_4$alkyl, or
$R_1$ is methyl or ethyl, especially methyl; or
$R_2$ and $R_3$ are independently of each other hydrogen or $C_1$-$C_4$alkyl; or
$R_2$ and $R_3$ is hydrogen, methyl or ethyl, preferably methyl; or
$R_2$ and $R_3$ are hydrogen; or
$R_4$ is aryl or heteroaryl, each optionally substituted with substituents selected from the group comprising alkyl, alkenyl, alkynyl, cycloalkyl, cycloalkyl-alkyl, phenyl and phenylalkyl, where all these groups may be substituted with one or more halogen atoms; alkoxy; alkenyloxy; alkynyloxy; alkoxyalkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl; or
$R_4$ is phenyl, naphthyl or thiophenyl, each optionally substituted by one to three substituents selected from the group comprising $C_1$-$C_8$alkyl, $C_2$-$C_8$alkenyl, $C_2$-$C_8$alkynyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfonyl, halogen, cyano, nitro and $C_1$-$C_8$alkoxycarbonyl; or
$R_4$ is phenyl, naphthyl, thiophenyl, each optionally substituted by one to three substituents selected from the group comprising $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, halogen, cyano, nitro and $C_1$-$C_8$alkoxycarbonyl; or
Further preferred subgroups are those wherein
$R_1$ is alkyl; and $R_4$ is aryl or heteroaryl, each optionally substituted by substituents selected from to group comprising alkyl, alkenyl, alkynyl, cycloalkyl, cycloalkyl-alkyl, phenyl and phenylalkyl, where all these groups may be substituted by one or several halogen; alkoxy; alkenyloxy; alkynyloxy; alkoxyalkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl; or
$R_2$ is hydrogen; and $R_1$ and $R_3$ are independently $C_1$-$C_6$alkyl; and $R_4$ is phenyl, naphthyl, 1,3-biphenyl or 1,4-biphenyl, each optionally substituted by one to three substituents selected from the group comprising $C_1$-$C_8$alkyl, $C_2$-$C_8$alkenyl, $C_2$-$C_8$alkynyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfonyl, halogen, cyano, nitro and $C_1$-$C_8$alkoxycarbonyl; or
$R_2$ is hydrogen; and $R_1$ and $R_3$ are each independently methyl or ethyl; and $R_4$ is phenyl, naphthyl, 1,3-biphenyl or 1,4-biphenyl, each optionally substituted by one to three substituents selected from the group comprising $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, halogen, cyano, nitro and $C_1$-$C_8$alkoxycarbonyl.

Other preferred subgroups of the compounds of formula I are those wherein
$R_1$ is $C_1$-$C_8$alkyl; and
$R_2$ and $R_3$ are independently of each other hydrogen or $C_1$-$C_4$alkyl; and R₄ is aryl or heteroaryl, each optionally substituted with substituents selected from to group comprising alkyl, alkenyl, alkynyl, cycloalkyl, cycloalkylalkyl, phenyl and phenylalkyl, where all these groups may be substituted with one or more substituents selected from the group comprising halogen; alkoxy, alkenyloxy, alkynyloxy; alkoxyalkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl; or wherein R₁ is $C_1$-$C_6$alkyl; and R₂ and R₃ is hydrogen, methyl or ethyl, preferably methyl; and R₄ is phenyl, naphthyl or biphenyl, each optionally substituted by one to three substituents selected from the group comprising $C_1$-$C_8$alkyl, $C_2$-$C_8$alkenyl, $C_2$-$C_8$alkynyl, $C_{1-C8}$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfonyl, halogen, cyano, nitro and $C_1$-$C_8$alkoxycarbonyl; or wherein R₁ is $C_1$-$C_4$alkyl, and R₂ and R₃ is hydrogen or methyl; and R₄ is phenyl, naphthyl, thiophenyl, each optionally substituted by one to three substituents selected from the group comprising $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, halogen, cyano, nitro and $C_1$-$C_8$alkoxycarbonyl; or wherein R₂ and R₃ are hydrogen; and R₁ is methyl or ethyl; and R₄ is phenyl, naphthyl, thiophenyl, each optionally substituted by one to three substituents selected from the group comprising $C_1$-$C_8$alkyl, $C_1$-$C_8$haloalkyl, $C_1$-$C_8$alkoxy, $C_1$-$C_8$halo-alkoxy, $C_1$-$C_8$alkylthio, $C_1$-$C_8$haloalkylthio, halogen, cyano, nitro and $C_1$-$C_8$alkoxycarbonyl.

Preferred individual compounds are:

2-hydroxy-2-(4-bromophenyl)-N-[2-(3-methoxy-4-hydroxyphenyl)-ethyl]-acetamide,
2-hydroxy-2-(4-chlorophenyl)-N-[2-(3-methoxy-4-hydroxyphenyl)-ethyl]-acetamide,
2-hydroxy-2-(3,4-dichlorophenyl)-N-[2-(3-methoxy-4-hydroxyphenyl)-ethyl]-acetamide,
2-hydroxy-2-biphenyl-4-yl-N-[2-(3-methoxy-4-hydroxyphenyl)-ethyl]-acetamide,
2-hydroxy-2-naphthalen-2-yl-N-[2-(3-methoxy-4-hydroxyphenyl)-ethyl]-acetamide,
2-hydroxy-2-p-tolyl-N-[2-(3-methoxy-4-hydroxyphenyl)-ethyl]-acetamide,
2-hydroxy-2-(4-ethylphenyl)-N-[2-(3-methoxy-4-hydroxyphenyl)-ethyl]-acetamide,
2-hydroxy-2-(4-trifluoromethylphenyl)-N-[2-(3-methoxy-4-hydroxyphenyl)-ethyl]-acetamide,
2-hydroxy-2-(4-fluorophenyl)-N-[2-(3-methoxy-4-hydroxyphenyl)-ethyl]-acetamide,
2-hydroxy-2-(3,4-difluorophenyl)-N-[2-(3-methoxy-4-hydroxyphenyl)-ethyl]-acetamide,
2-hydroxy-2-(4-chloro-3-fluorophenyl)-N-[2-(3-methoxy-4-hydroxyphenyl)-ethyl]-acetamide,
2-hydroxy-2-(3-chloro-4-fluorophenyl)-N-[2-(3-methoxy-4-hydroxyphenyl)-ethyl]-acetamide.
2-hydroxy-2-(5-chlorothiophen-2-yl)-N-[2-(4-hydroxy-3-methoxyphenyl)-ethyl]-acetamide,
2-hydroxy-2-phenyl-N-[2-(4-hydroxy-3-methoxyphenyl)-ethyl]-acetamide, and
2-hydroxy-2-(4-methoxyphenyl)-N-[2-(4-hydroxy-3-methoxyphenyl)-ethyl]-acetamide, and the R- and S-enantiomers of these compounds, for example (R)-2-hydroxy-2-(4-bromophenyl)-N-[2-(3-methoxy-4-hydroxyphenyl)-ethyl]-acetamide,
(S)-2-hydroxy-2-(4-bromophenyl)-N-[2-(3-methoxy-4-hydroxyphenyl)-ethyl]-acetamide,
(R)-2-hydroxy-2-(4-chlorophenyl)-N-[2-(3-methoxy-4-hydroxyphenyl)-ethyl]-acetamide,
(S)-2-hydroxy-2-(3,4-dichlorophenyl)-N-[2-(3-methoxy-4-hydroxyphenyl)-ethyl]-acetamide,
(S)-2-hydroxy-2-(4-chlorophenyl)-N-[2-(3-methoxy-4-hydroxyphenyl)-ethyl]-acetamide,
(R)-2-hydroxy-2-(3,4-dichlorophenyl)-N-[2-(3-methoxy-4-hydroxyphenyl)-ethyl]-acetamide,
(R)-2-hydroxy-2-biphenyl-4-yl-N-[2-(3-methoxy-4-hydroxyphenyl)-ethyl]-acetamide,
(S)-2-hydroxy-2-naphthalen-2-yl-N-[2-(3-methoxy-4-hydroxyphenyl)-ethyl]-acetamide,
(S)-2-hydroxy-2-biphenyl-4-yl-N-[2-(3-methoxy-4-hydroxyphenyl)-ethyl]-acetamide,
(R)-2-hydroxy-2-naphthalen-2-yl-N-[2-(3-methoxy-4-hydroxyphenyl)-ethyl]-acetamide,
(R)-2-hydroxy-2-p-tolyl-N-[2-(3-methoxy-4-hydroxyphenyl)-ethyl]-acetamide,
(S)-2-hydroxy-2-(4-ethylphenyl)-N-[2-(3-methoxy-4-hydroxyphenyl)-ethyl]-acetamide,
(S)-2-hydroxy-2-p-tolyl-N-[2-(3-methoxy-4-hydroxyphenyl)-ethyl]-acetamide,
(R)-2-hydroxy-2-(4-ethylphenyl)-N-[2-(3-methoxy-4-hydroxyphenyl)-ethyl]-acetamide,
(R)-2-hydroxy-2-(4-trifluoromethylphenyl)-N-[2-(3-methoxy-4-hydroxyphenyl)-ethyl]-acetamide,
(S)-2-hydroxy-2-(4-trifluoromethylphenyl)-N-[2-(3-methoxy-4-hydroxyphenyl)-ethyl]-acetamide,
(R)-2-hydroxy-2-(4-fluorophenyl)-N-[2-(3-methoxy-4-hydroxyphenyl)-ethyl]-acetamide,
(S)-2-hydroxy-2-(4-fluorophenyl)-N-[2-(3-methoxy-4-hydroxyphenyl)-ethyl]-acetamide,
(R)-2-hydroxy-2-(3,4-difluorophenyl)-N-[2-(3-methoxy-4-hydroxyphenyl)-ethyl]-acetamide,
(S)-2-hydroxy-2-(3,4-difluorophenyl)-N-[2-(3-methoxy-4-hydroxyphenyl)-ethyl]-acetamide,
(R)-2-hydroxy-2-(4-chloro-3-fluorophenyl)-N-[2-(3-methoxy-4-hydroxyphenyl)-ethyl]-acetamide,
(S)-2-hydroxy-2-(4-chloro-3-fluorophenyl)-N-[2-(3-methoxy-4-hydroxyphenyl)-ethyl]-acetamide,
(R)-2-hydroxy-2-(3-chloro-4-fluorophenyl)-N-[2-(3-methoxy-4-hydroxyphenyl)-ethyl]-acetamide.
(S)-2-hydroxy-2-(3-chloro-4-fluorophenyl)-N-[2-(3-methoxy-4-hydroxyphenyl)-ethyl]-acetamide.
(R)-2-hydroxy-2-(5-chlorothiophen-2-yl)-N-[2-(4-hydroxy-3-methoxyphenyl)-ethyl]-acetamide,
(S)-2-hydroxy-2-(5-chlorothiophen-2-yl)-N-[2-(4-hydroxy-3-methoxyphenyl)-ethyl]-acetamide,
(R)-2-hydroxy-2-phenyl-N-[2-(4-hydroxy-3-methoxyphenyl)-ethyl]-acetamide,
(S)-2-hydroxy-2-phenyl-N-[2-(4-hydroxy-3-methoxyphenyl)-ethyl]-acetamide,
(R)-2-hydroxy-2-(4-methoxyphenyl)-N-[2-(4-hydroxy-3-methoxyphenyl)-ethyl]-acetamide, and
(S)-2-hydroxy-2-(4-methoxyphenyl)-N-[2-(4-hydroxy-3-methoxyphenyl)-ethyl]-acetamide.

The novel species of the above list have especially been prepared in the context of this invention and thus form another embodiment thereof. Preferred species are selected from the following group:

2-hydroxy-2-(4-bromophenyl)-N-[2-(3-methoxy-4-hydroxyphenyl)-ethyl]-acetamide, 2-hydroxy-2-(4-chlorophenyl)-N-[2-(3-methoxy-4-hydroxyphenyl)-ethyl]-acetamide,
2-hydroxy-2-(3,4-dichlorophenyl)-N-[2-(3-methoxy-4-hydroxyphenyl)-ethyl]-acetamide,
2-hydroxy-2-p-tolyl-N-[2-(3-methoxy-4-hydroxyphenyl)-ethyl]-acetamide,
2-hydroxy-2-(4-ethylphenyl)-N-[2-(3-methoxy-4-hydroxyphenyl)-ethyl]-acetamide,
2-hydroxy-2-(4-trifluoromethylphenyl)-N-[2-(3-methoxy-4-hydroxyphenyl)-ethyl]-acetamide,
2-hydroxy-2-(4-fluorophenyl)-N-[2-(3-methoxy-4-hydroxyphenyl)-ethyl]-acetamide,
2-hydroxy-2-(3,4-difluorophenyl)-N-[2-(3-methoxy-4-hydroxyphenyl)-ethyl]-acetamide,
2-hydroxy-2-(4-chloro-3-fluorophenyl)-N-[2-(3-methoxy-4-hydroxyphenyl)-ethyl]-acetamide,
2-hydroxy-2-(3-chloro-4-fluorophenyl)-N-[2-(3-methoxy-4-hydroxyphenyl)-ethyl]-acetamide.
2-hydroxy-2-(5-chlorothiophen-2-yl)-N-[2-(4-hydroxy-3-methoxyphenyl)-ethyl]-acetamide,
2-hydroxy-2-phenyl-N-[2-(4-hydroxy-3-methoxyphenyl)-ethyl]-acetamide, and
2-hydroxy-2-(4-methoxyphenyl)-N-[2-(4-hydroxy-3-methoxyphenyl)-ethyl]-acetamide, and the R- and S-enantiomers of these compounds, for example
(R)-2-hydroxy-2-(4-bromophenyl)-N-[2-(3-methoxy-4-hydroxyphenyl)-ethyl]-acetamide,
(S)-2-hydroxy-2-(4-bromophenyl)-N-[2-(3-methoxy-4-hydroxyphenyl)-ethyl]-acetamide,
(R)-2-hydroxy-2-(4-chlorophenyl)-N-[2-(3-methoxy-4-hydroxyphenyl)-ethyl]-acetamide,
(S)-2-hydroxy-2-(3,4-dichlorophenyl)-N-[2-(3-methoxy-4-hydroxyphenyl)-ethyl]-acetamide,
(S)-2-hydroxy-2-(4-chlorophenyl)-N-[2-(3-methoxy-4-hydroxyphenyl)-ethyl]-acetamide,
(R)-2-hydroxy-2-(3,4-dichlorophenyl)-N-[2-(3-methoxy-4-hydroxyphenyl)-ethyl]-acetamide,
(R)-2-hydroxy-2-p-tolyl-N-[2-(3-methoxy-4-hydroxyphenyl)-ethyl]-acetamide,
(S)-2-hydroxy-2-p-tolyl-N-[2-(3-methoxy-4-hydroxyphenyl)-ethyl]-acetamide,
(R)-2-hydroxy-2-(4-ethylphenyl)-N-[2-(3-methoxy-4-hydroxyphenyl)-ethyl]-acetamide,
(S)-2-hydroxy-2-(4-ethylphenyl)-N-[2-(3-methoxy-4-hydroxyphenyl)-ethyl]-acetamide,
(R)-2-hydroxy-2-(4-trifluoromethylphenyl)-N-[2-(3-methoxy-4-hydroxyphenyl)-ethyl]-acetamide,
(S)-2-hydroxy-2-(4-trifluoromethylphenyl)-N-[2-(3-methoxy-4-hydroxyphenyl)-ethyl]-acetamide,
(R)-2-hydroxy-2-(4-fluorophenyl)-N-[2-(3-methoxy-4-hydroxyphenyl)-ethyl]-acetamide,
(S)-2-hydroxy-2-(4-fluorophenyl)-N-[2-(3-methoxy-4-hydroxyphenyl)-ethyl]-acetamide,
(R)-2-hydroxy-2-(3,4-difluorophenyl)-N-[2-(3-methoxy-4-hydroxyphenyl)-ethyl]-acetamide,
(S)-2-hydroxy-2-(3,4-difluorophenyl)-N-[2-(3-methoxy-4-hydroxyphenyl)-ethyl]-acetamide,
(R)-2-hydroxy-2-(4-chloro-3-fluorophenyl)-N-[2-(3-methoxy-4-hydroxyphenyl)-ethyl]-acetamide,
(S)-2-hydroxy-2-(4-chloro-3-fluorophenyl)-N-[2-(3-methoxy-4-hydroxyphenyl)-ethyl]-acetamide,
(R)-2-hydroxy-2-(3-chloro-4-fluorophenyl)-N-[2-(3-methoxy-4-hydroxyphenyl)-ethyl]-acetamide.
(S)-2-hydroxy-2-(3-chloro-4-fluorophenyl)-N-[2-(3-methoxy-4-hydroxyphenyl)-ethyl]-acetamide,
(R)-2-hydroxy-2-(5-chlorothiophen-2-yl)-N-[2-(4-hydroxy-3-methoxyphenyl)-ethyl]-acetamide,
(S)-2-hydroxy-2-(5-chlorothiophen-2-yl)-N-[2-(4-hydroxy-3-methoxyphenyl)-ethyl]-acetamide,
(R)-2-hydroxy-2-phenyl-N-[2-(4-hydroxy-3-methoxyphenyl)-ethyl]-acetamide,
(S)-2-hydroxy-2-phenyl-N-[2-(4-hydroxy-3-methoxyphenyl)-ethyl]-acetamide,
(R)-2-hydroxy-2-(4-methoxyphenyl)-N-[2-(4-hydroxy-3-methoxyphenyl)-ethyl]-acetamide, and
(S)-2-hydroxy-2-(4-methoxyphenyl)-N-[2-(4-hydroxy-3-methoxyphenyl)-ethyl]-acetamide.

The present invention further relates to processes for the preparation of 2-(3-alkoxy-4-hydroxyphenyl)-ethylamines of the formula II.

It is known from Japanese Patent Specification JP 55-45604 to prepare 2-(4-hydroxyphenyl)-nitroethanes by transforming an optionally substituted 4-hydroxybenzaldehyde with nitromethane into a corresponding 1-(4-hydroxyphenyl)-2-nitroethene and reducing the latter with a metal hydride, such as sodium borohydride or lithium aluminum hydride according to the following reaction scheme:

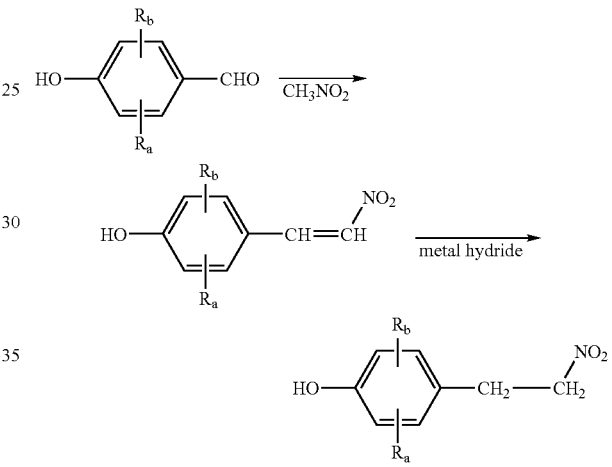

$R_a$ and $R_b$ are hydrogen, halogen, lower alkoxy, lower alkyl or lower alkenyl The 2-(4-hydroxyphenyl)-nitroethanes thus obtained are used as intermediates for the preparation of the corresponding 2-(4-hydroxyphenyl)-acetic acids.

Further, it is known from Tetrahedron Letters (15) 1317-20 (1977) to prepare phenethylamines by reducing nitrostyrenes with sodium boron hydride to 2-phenylnitroethanes and further reducing the latter with Al/Hg in aqueous methanol. Specifically described is the reduction of 3-methoxy-4-benzyloxystyrene to 2-(3-methoxy-4-benzyloxyphenyl)-ethylamine. This reaction sequence can be described by the following reaction scheme:

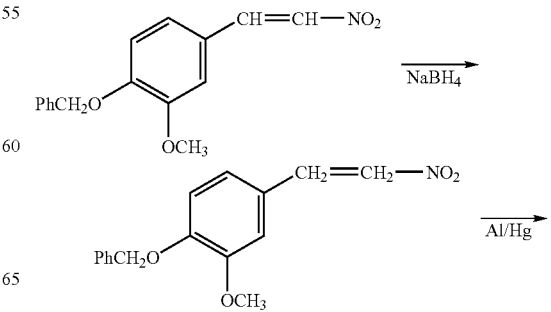

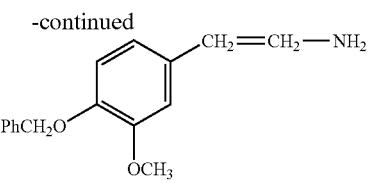

From Tetrahedron Letters 51(8), 2305-24, 1993 it is further known to prepare enantio-enriched 2-aryl-alkylamines by addition of primary dialkylzinc reagents to 2-aryl-nitroolefines and subsequently reducing the 2-aryl-nitroalkanes thus obtained by catalytic hydrogenation over Pd/C or Raney-Ni.

It is further known from Chem. Ber. 55, 3388, (1933) and 71, 2154 (1938) to prepare 2-phenylethylamines by reacting a substituted benzaldehyde with hydrogen cyanide to form the corresponding mandelonitrile and reducing the latter to the corresponding 2-phenylethylamine. The reduction is carried out by catalytic hydrogenation with platinum oxide as catalyst. The transformation of substituted mandelonitriles into the corresponding 2-phenylethylamines by catalytic hydrogenation with platinum oxide (Adams catalyst) is also described in J. Amer. Chem. Soc. 55, 2593-2597, 1933.

According to a first alternative the 2-(3-alkoxy-4-hydroxyphenyl)-ethylamines of the formula II

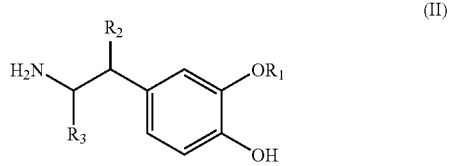

wherein $R_1$, $R_2$ and $R_3$ are as defined above are prepared by a process which comprises the steps of:

$a_1$) reacting a nitrostyrene of the formula VI

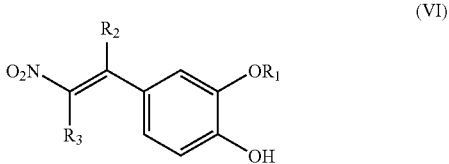

wherein $R_1$, $R_2$ and $R_3$ are as defined above, with reducing agent to form a 2-phenyl-nitroethane derivative of the formula VII,

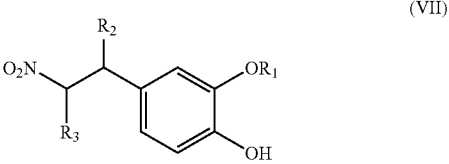

wherein $R_1$ $R_2$ and $R_3$ are as defined above; and $b_1$) further reacting the 2-phenyl-nitroethane derivative of the formula VII obtained in step a) with hydrogen in the presence of a catalyst to form a 2-phenylethylamine derivative of the formula II.

Steps $a_1$) and $b_1$) are further described in detail as follows.

Step $a_1$

Suitable reducing agents for the reduction of a nitrostyrene of the formula VI to a 2-phenyl-nitroethane of the formula VII are metal hydrides, such as sodium borohydride and lithium borohydride. Other suitable reducing agents are 2,6,dialkyl-3,5-di-alkoxycarbonyl-1,4-di-hydropyridines, particularly 2,6-dimethyl-3,5-di-ethoxycarbonyl-1,4-dihydropyridine (Hantzsch-ester). Further suitable reducing agents are boranes and trialkylborohydrides. Preferably sodium borohydride is used for the reduction of the nitrostyrene of the formula VI. For enantiomerically enriched 2-phenyl-nitroethanes of the formula VII asymmetric catalysts for chiral reduction can be used. The reduction reaction is advantageously performed in a inert solvent, such as aromatic and aliphatic or halogenated hydrocarbons. Suitable solvents are chlorohydrocarbons, such as dichloromethane or chlorobenzene, hydrocarbons, such as n-hexane, cyclohexane or toluene, ethers, such as diethylether, tert.-butyl-methy ether, dioxane or tetrahydrofuran, alcohols, such as methanol, ethanol, propanol, isopropanol or sec. butanol. Mixtures of the afore-mentioned solvents can also be used. The reduction reaction can be performed at a temperature of from −80° C. to +150° C., with temperatures within the range of −20° C. to +60° C. being preferred. The 2-phenyl-nitroethanes of the formula VII are novel compounds and are, therefore, also part of the present inventive concept.

Step $b_1$

Suitable catalysts for the hydrogenation of a 2-phenyl-nitroethane of the formula VII to a 2-(3-alkoxy-4-hydroxyphenyl)-ethylamines of the formula II are, for example, Raney-nickel, palladium on a suitable carrier, such as palladium on carbon. Further, the reduction of 2-phenyl-nitroethanes of the formula VII can also be carried out by reaction with hydrogen donors, such as hydrazine. The reduction reaction is advantageously performed in an inert solvent, such as water or alcohols, such as methanol, ethanol, propanol, isopropanol or sec. butanol. Further suitable solvents are chlorohydrocarbons, such as dichloromethane, and chlorobenzene, hydrocarbons, such as n-hexane, cyclohexane and toluene, ethers, such as diethylether, tert-butyl-methyl ether, dioxane and tetrahydrofuran, carboxylic acids, such as acetic acid. Mixtures of the afore-mentioned solvents can also be used. The reduction reaction can be performed under neutral or acidic conditions. The reduction reaction can be performed at a temperature of from −20° C. to +150° C., with temperatures within the range of from 0° C. to +100° C. being preferred.

The nitrostyrenes of the formula IV can be prepared by reacting a carbonyl compound of the formula VIII

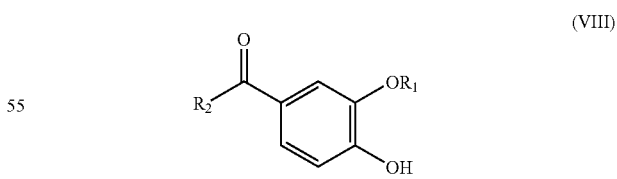

wherein $R_1$ and $R_2$ are as defined for formula I, with a nitroalkane of the formula X

wherein $R_3$ is as defined for formula I. This reaction can be carried out under conditions as described in Japanese Patent Specification JP 55-45604.

According to a second alternative the 2-(3-alkoxy-4-hydroxyphenyl)-ethylamines of the formula II

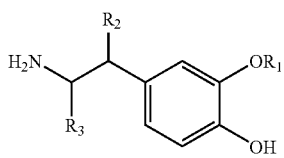
(II)

wherein $R_1$ $R_2$ and $R_3$ are as defined above are prepared by a process which comprises the steps of:

a$_2$) reacting a carbonyl compound of the formula VIII

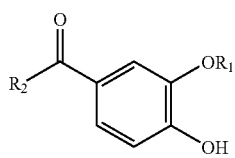
(VIII)

wherein $R_1$ and $R_2$ are as defined above, with hydrogen cyanide to form an α-hydroxynitrile of the formula IX

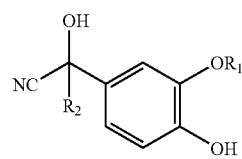
(IX)

wherein $R_1$ and $R_2$ are as defined above, and b$_2$) further reacting the α-hydroxynitrile of the formula VII with hydrogen in the presence of a catalyst to form a 2-(3-alkoxy-4-hydroxyphenyl)-ethylamine of the formula II.

Most of the compounds of the formula VIII are known compounds and can be prepared by conventional methods.

The reactions involved in steps a$_2$) and b$_2$) are further described in detail as follows:

Step a$_2$

Suitable agents for the conversion of a compound of the formula VIII into a 2-phenyl-cyanohydrin derivative of the formula IX are prussic acid (hydrogen cyanide) and any kind of salts thereof as well as reactive cyanohydrins, for example acetone cyanohydrin. The reaction is advantageously performed under neutral to acidic conditions. Suitable acids are carboxylic acids, hydrochloric acid, sulfuric acid, optionally substituted alkyl or aryl sulfonic acids, phosphoric acid and nitric acid, with hydrochloric acid and sulfuric acid being preferred.

Optionally, the reaction can be performed in the presence of a biocatalyst to produce the optically enriched cyanohydrin derivatives of the formula VII. Optionally, the reaction can be performed in the presence of an alkylating or acylating agent, e.g. like acetyl chloride or ethyl chloroformate to yield protected 2-phenyl-cyanohydrin derivative of the formula IX.

The reaction is advantageously performed in a solvent selected from water, alcohols, hydrocarbons, chorohydrocarbons, ethers and nitrites. Especially suitable solvents are alcohols, such as methanol, ethanol, propanol, isopropanol or sec. butanol, chlorohydrocarbons, such as dichloromethane or chlorobenzene, hydrocarbons, such as n-hexane, cyclohexane or toluene, ethers, such as diethylether, tert-butyl-methyl ether, dioxane or tetrahydrofuran, nitrites, such as acetonitrile or butyronitrile. Mixtures of the afore-mentioned solvents can also be used. If aprotic solvents are used, the reaction is advantageously performed in the presence of a phase transfer catalyst. The reaction can be performed at a temperature of from −80° C. to +150° C., with temperatures within the range of −20° C. to +60° C. being preferred.

Step b$_2$

Suitable catalysts for the hydrogenation of a 2-phenyl-cyanohydrin derivative of the formula IX are, for example, platinum oxide, Raney-nickel, palladium on a suitable carrier, such as palladium on carbon. The reduction reaction is advantageously performed in a inert solvent, such as water, alcohols, hydrcarbons, halogenated hydrocarbons,ethers or carboxylic acids. Especially suitable solvents are alcohols, such as methanol, ethanol, propanol, isopropanol or sec. butanol. Other suitable solvents are chlorohydrocarbons, such as dichloromethane or chlorobenzene, hydrocarbons, such as n-hexane, cyclohexane or toluene, ethers, such as diethylether, tert-butyl-methy ether, dioxane or tetrahydrofuran, carboxylic acids, such as acetic acid. Mixtures of the afore-mentioned solvents can also be used. The reduction reaction can be performed under neutral or acidic conditions. Suitable acids are those mentioned for step a$_2$). The reduction reaction can be performed at a temperature of from −20° C. to +150° C., with temperatures within the range of 0° C. to +100° C. being preferred.

The hydrogenation can be either performed with an isolated 2-phenyl-cyanohydrin of the formula IX or in situ without isolation of the 2-phenyl-cyanohydrin of the formula I formed in step a$_2$). Preferably, the hydrogenation is performend with in a manner such that a 2-phenyl-cyanohydrin of the formula IX is introduced portionwise into the reaction mixture in order to minimise the formation of free hydrogen cyanide which detrimentally affects the activity of the catalyst. This equally applies to the use of an isolated 2-phenyl-cyanohydrin derivative of the formula IX and the use of a solution of the 2-phenyl-cyanohydrin derivative of the formula IX obtained in step a$_2$). The performance of the hydrogenation in this manner makes it possible to reduce the amount of catalyst. Further, the yield per volume can be increased by up to 20%.

The compounds of the formula I are valuable intermediates which can be used for the preparation of fungicidally active compounds which represent a sub group of the compounds of the above formula Ia which sub group can be defined by formula Ib

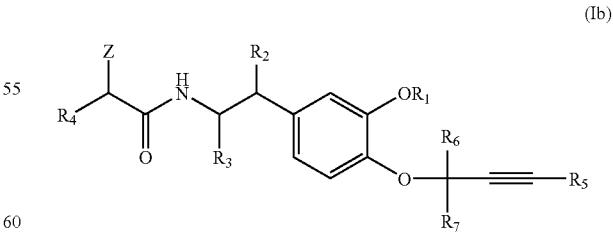
(Ib)

wherein $R_1$ is alkyl, $R_2$ and $R_3$ are each independently hydrogen or alkyl, and $R_4$ is optionally substituted aryl or optionally substituted heteroaryl, R₅ is hydrgen, alkyl, cycloalkyl or optionally substituted aryl,
R₆ and R₇ are each independently of each other hydrogen or alkyl, and Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl, and of the enantiomers thereof.

The present invention is further illustrated but in no way limited by the following examples.

E1: Preparation of 2-Phenyl-2-hydroxy-N-[2-(4-hydroxy-3-methoxyphenyl)-ethyl]-acetamides

E1.1: 2-(4-Bromophenyl)-2-hydroxy-N-[2-(4-hydroxy-3-methoxyphenyl)-ethyl]-acetamide by solvent process

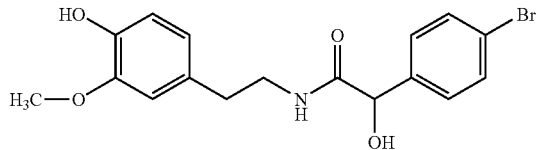

5-(4-Bromophenyl)-2,2-dimethyl-1,3-dioxolan-4-one (15 g; 55 mmol) is dissolved in 50 ml of methanol. 4-(2-Aminoethyl)-2-methoxyphenol hydrochloride (14 g; 69 mmol) and triethylamine (7 g; 69 mmol) are added and the mixture is stirred for 72 hours at room temperature. The solvent is removed in vacuum and the residue is extracted with ethyl acetate and the combined organic phases are washed with brine, dried over sodium sulfate and evaporated to dryness. The remaining 2-(4-bromophenyl)-2-hydroxy-N-[2-(4-hydroxy-3-methoxyphenyl)-ethyl]-acetamide is purified by chromatography on silica gel.

¹H-NMR (300 MHz, CDCl₃): 2.71 (t, 2H, CH₂CH₂), 3.54 (t, 2H, CH₂CH₂), 3.80 (s, 3H, OCH₃), 5.39 (s, 1H, CHOH), 6.16 (bs, 1H, NH), 6.52-7.35 (m, 7H, CH arom.).

E1.2: 2-(4-Chlorophenyl)-2-hydroxy-N-[2-(4-hydroxy-3-methoxyphenyl)-ethyl]-acetamide

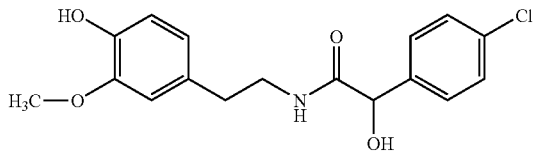

a) by solvent process 5-(4-Chlorophenyl)-2,2-dimethyl-1,3-dioxolan-4-one (5.67 g; 25 mmol) and 4-(2-aminoethyl)-2-methoxyphenol (4.39 g; 26.25 mmol) are dissolved in 31.25 g of dry dioxane. The mixture is heated to reflux (+100° C.) and the solution is stirred for 7 hours at reflux temperature. The solvent is removed in vacuum and to the residue 20 g of a 1:1 mixture of ethyl acetate and hexane is added at +70° C. whereupon a precipitate is formed. After cooling, filtering and washing the product is dried in vacuum. 7.44 g of 2-(4-chlorophenyl)-2-hydroxy-N-[2-(4-hydroxy-3-methoxyphenyl)-ethyl]-acetamide with a purity of 91.0% is obtained in 80.6% yield.

¹H-NMR (300 MHz, CDCl₃): 2.72 (q, 2H, CH₂CH₂), 3.50 (m, 2H, CH₂CH₂), 3.82 (s, 3H, OCH₃), 4.95 (s,1H, CHOH), 6.23 (bs,₁H, NH), 6.49-7.35 (m, 7H, CH arom.).

b) by melt process (4-Chloro-phenyl)-hydroxy-acetic acid methyl ester (10.03 g; 50 mmol) and 4-(2-aminoethyl)-2-methoxyphenol (4.39 g; 26.25 mmol) are weighed into a 50 ml reactor. The mixture is heated to +120° C. under nitrogen. After approximately 10 to 30 minutes a homogeneous mixture is formed and methanol is distilled out of the reactor. The mixture is then stirred for 3 to 5 hours until the conversion is complete (>95%). Upon cooling to below +95° C. the mixture crystallizes spontaneously yielding the product in almost quantitative yield. The 2-(4-chlorophenyl)-2-hydroxy-N-[2-(4-hydroxy-3-methoxyphenyl)-ethyl]-acetamide can be recrystallized from ethyl acetate/hexane mixture in analogy to the previous experiment or used as is (i.e. as a solution in a suitable solvent) for the next step.

According to the above procedures the compounds listed in Table E1 are obtained.

TABLE E1

| No. | R' | R" | Physical data |
|---|---|---|---|
| E4.01 | 4-Br | 3-OCH₃ | ¹H-NMR(300MHz,CDCl₃): 2.71(t, 2H, CH₂CH₂), 3.54(t, 2H, CH₂CH₂), 3.80(s, 3H, OCH₃), 5.39(s, 1H, CHOH), 6.16(bs, 1H, NH), 6.52-7.35(m, 7H, CH arom.) |
| E4.02 | 4-Cl | 3-OCH₃ | ¹H-NMR(300MHz,CDCl₃): 2.73(t, 2H, CH₂CH₂), 3.51(t, 2H, CH₂CH₂), 3.84(s, 3H, OCH₃), 4.97(S, 1H, CHOH), 6.18(bs, 1H, NH), 6.53-7.32(m, 7H, CH arom.) |
| E4.03 | 4-CH₃ | 3-OCH₃ | m.p. 77-78° C. |
| E4.04 | 4-F | 3-OCH₃ | m.p. 96-98° C. |
| E4.05 | 4-C₂H₅ | 3-OCH₃ | ¹H-NMR(300MHz,CDCl₃): 1.15(t, 3H, CH₃), 2.57(q, 2H, CH₂), 2.6-2.7(m, 2H, CH₂) 3.74(s, 3H, OCH₃), 4.88(s, 1H, CHO), 5.5 (s, 1H, OH) 6.05(1, 1H, NH), 6.3-7.2(m, 7H, OH arom.) |
| E4.06 | 3,4-di-Cl | 3-OCH₃ | ¹H-NMR(300MHz,CDCl₃): 2.65-2.8(m, 2H, CH₂), 3.4-3.6(m, 2H, CH₂), 3.82(s, 3H, OCH₃), 3.88(d, 1H, CHO); 5.6(s, 1H, OH), 6.45(t, 1H, NH), 6.5-7.5(m, 6H, OH arom.) |

TABLE E1-continued

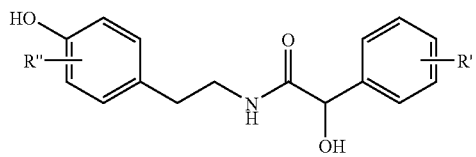

| No. | R' | R" | Physical data |
|---|---|---|---|
| E4.07 | H | 3-OCH$_3$ | $^1$H-NMR(300MHz,CDCl$_3$): 2,72(t, 2H, CH$_2$), 3,5(q, 2H, CH$_2$), 3,83(s, 3H, OCH$_3$), 4,98(d, 1H, CHO), 5,62(s, 1H, OH), 6,22(s, 1H, NH) 6,43-7,38(m, 8H, CH arom.) |
| E4.08 | 4-Br | 3-OCH$_3$ | (R)-form |
| E4.09 | 4-Cl | 3-OCH$_3$ | (R)-form |
| E4.10 | 4-CH$_3$ | 3-OCH$_3$ | (R)-form |
| E4.11 | 4-F | 3-OCH$_3$ | (R)-form |
| E4.12 | 4-C$_2$H$_5$ | 3-OCH$_3$ | (R)-form |
| E4.13 | 3,4-di-Cl | 3-OCH$_3$ | (R)-form |
| E4.14 | H | 3-OCH$_3$ | (R)-form |
| E4.15 | 4-Br | 3-OCH$_3$ | (S)-form |
| E4.16 | 4-Cl | 3-OCH$_3$ | (S)-form |
| E4.17 | 4-CH$_3$ | 3-OCH$_3$ | (S)-form |
| E4.18 | 4-F | 3-OCH$_3$ | (S)-form |
| E4.19 | 4-C$_2$H$_5$ | 3-OCH$_3$ | (S)-form |
| E4.20 | 3,4-di-Cl | 3-OCH$_3$ | (S)-form |
| E4.21 | H | 3-OCH$_3$ | (S)-form |

E2: Preparation of 2-(4-chlorophenyl)-2-hydroxyacetic acid methyl ester

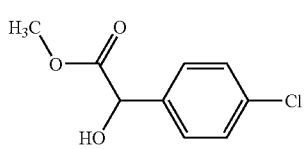

2-(4-Chlorophenyl)-2-hydroxyacetic acid (40 g; 0.2 mol) is dissolved in 100 ml of methanol and stirred at +20° C. At this temperature 5 ml of concentrated sulfuric acid are added dropwise. After the addition is complete the reaction mixture is heated up to +45° C. and stirred for further 30 minutes. Then the reaction mixture is poured into a cooled (0° C.) solution of sodium carbonate (42 g; 0.4 mol) in 300 ml of water. The product is extracted with toluene (3×50 ml) washed with brine (3×50 ml) dried (Na$_2$SO4) and evaporated. After crystallization from diethylether/hexane (10 g/80 g) 2-(4-chlorophenyl)-2-hydroxyacetic acid methylester (34 g; 84% yield) is obtained as a colorless solid. M.p. 54-55° C.

E3: Preparation of 5-(4-bromophenyl)-2,2-dimethyl-[1,3]dioxolan-4-one

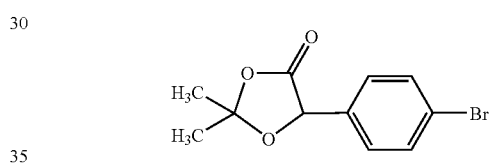

2-(4-Bromophenyl)-2-hydroxyacetic acid (97 g; 0,42 mol) is dissolved in 200 ml of acetone and the solution is cooled to –10° C. At this temperature 23 ml of concentrated sulfuric acid are added dropwise. After the addition is complete the reaction mixture is stirred at –10° C. for further 30 minutes and is subsequently poured into a cooled (0° C.) solution of sodium carbonate (86 g; 0,81 mol) in 800 ml of water. The crystalline 5-(4-bromophenyl)-2,2-dimethyl-1,3-dioxolan-4-one is filtered, washed with ice-cold water and dried in the high vacuum.

$^1$H-NMR (300 MHz, CDCl$_3$): 1.72 (s, 3H, CH$_3$), 1.76 (s, 3H, CH$_3$), 5.37 (s, 1H, CHO), 7.37 (d, 2H, CH arom.).

According to the procedure of example E3 the compounds listed in table E3 are obtained:

TABLE E3

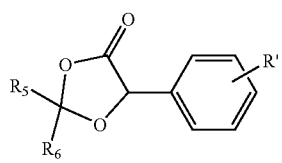

| No. | R' | R$_1$ | R$_2$ | Physical data |
|---|---|---|---|---|
| E3.1 | 4-Br | CH$_3$ | CH$_3$ | $^1$H-NMR(300MHz,CDCl$_3$): 1.72(s, 3H, CH$_3$), 1.76(s, 3H, CH$_3$), 5.37(s, 1H, CHO), 7.37(d, 2H, CH arom.). |
| E3.2 | 4-Cl | CH$_3$ | CH$_3$ | $^1$H-NMR(300MHz,CDCl$_3$): 1.69(s, 3H, CH$_3$), 1.74(s, 3H, CH$_3$), 5.39(s, 1H, CHO), 7.38-7.47(m, 4H, CH arom.). |
| E3.3 | 4-CH$_3$ | CH$_3$ | CH$_3$ | m.p. 53-54° C. |

TABLE E3-continued

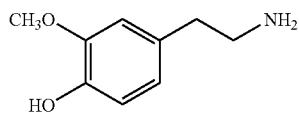

| No. | R' | $R_1$ | $R_2$ | Physical data |
|---|---|---|---|---|
| E3.4 | 4-F | $CH_3$ | $CH_3$ | m.p. 63-65° C. |
| E3.5 | 4-$C_2H_5$ | $CH_3$ | $CH_3$ | oil |
| E3.6 | 3,4-di-Cl | $CH_3$ | $CH_3$ | $^1$H-NMR(300MHz,CDCl$_3$): 1.68(s, 3H, CH$_3$), 1.72(s, 3H, CH$_3$), 5.35(s, 1H, CHO), 7.25-7.60(m, 3H, CH arom.). |
| E3.7 | H | $CH_3$ | $CH_3$ | |

E4: Preparation of 2-(methoxy-4-(2-nitroethyl)-phenol by reduction of 2-methoxy-4-(2-nitro-vinyl)-phenol E4.1: 2-Methoxy-4-(2-nitroethyl)-phenol

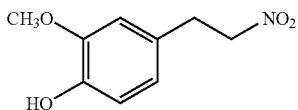

a) To sodium borohydride (4.3 g) suspended in a mixture of dioxane (85 ml) and ethanol (25 ml) at +10 to +15° C. is added 2-methoxy-4-(2-nitro-vinyl)-phenol in a mixture of dioxane (110 ml) and ethanol (50 ml). Thereafter the reaction mixture is stirred at room temperature for 2 hours. Acetic acid (4.5 ml) in water (130 ml) is then added carefully. The resulting mixture is evaporated to at about half of its volume. It is extracted with ethyl acetate (2×500 ml) washed with brine (2×100 ml) dried (MgSO$_4$) and evaporated. 2-methoxy-4-(2-nitro-ethyl)-phenol is obtained as an oil which is purified by flash column chromatography on silica gel using ethyl acetate/hexane (1:1).

$^1$H-NMR (CDCl$_3$) δ(ppm): 3.25 (t, 2H); 3.9 (s, 3H);4.6 (t, 2H); 5.65 (s,1H); 6.6-6.75 (m, 2H); 6.8-6.9 (m, 1H).

b) To sodium borohydride (1.93 g, 51.2 mmol) suspended in ethanol (15 ml) at +10 to +15° C. is added a solution of 2-methoxy-4-(2-nitro-vinyl)-phenol (10.0 g, 51.2 mmol) in tetrahydrofuran (100 ml) over 1 h. Thereafter the reaction mixture is stirred at room temperature for 30 minutes. Acetic acid (4 ml) in water (100 ml) is then added carefully. The resulting mixture is evaporated to at about a quarter of its volume. It is extracted with ethyl acetate (1×100 ml, 1×50 ml) washed with brine (2×50 ml) dried (Na$_2$SO$_4$) and evaporated. 2-methoxy-4-(2-nitro-ethyl)-phenol (9.64 g) is obtained as an oil, which is purified by kugelrohr distillation (+150° C., 0.02 torr) yielding 7.3 g (72%) of purified material.

E4.2: 4-(2-Amino-ethyl)-2-methoxy-phenol

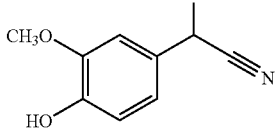

To 2-methoxy-4-(2-nitro-ethyl)-phenol (2.0 g) and Raney-nickel (3.7 g) in ethanol (30 ml) is added hydrazine hydrate (3.8 g) during 30 minutes. The reaction mixture is stirred for 1 hour at room temperature. After filtration the reaction mixture is poured into water (350 ml). It is extracted with ethyl acetate (2×400 ml) washed with brine (2×50 ml) dried (Na$_2$SO$_4$) and evaporated. 4-(2-amino-ethyl)-2-methoxy-phenol is obtained as colorless crystals.

$^1$H-NMR (d$_6$-DMSO) δ(ppm): 2.3-2.4 (m, 2H together with DMSO); 2.5 (t, 2H); 2.5-3.6 (broad, 3H together with H$_2$O); 3.5 (s, 3H); 6.-6.6 (m, 3H).

E5: Preparation of 2-(methoxy-4-(2-aminoethyl)-phenol by reduction of hydroxy-(4-hydroxy-3-methoxyphenyl)-acetonitrile E5.1: Hydroxy-(4-hydroxy-3-methoxyphenyl)-acetonitrile Sodium cyanide (10.2 g) is dissolved in water (40 ml) and cooled to 0° C. A second solution comprising vanillin (15.5 g) and ethanol (30 ml) is added at 0° C. Now, concentrated hydrochloric acid (28.5 g 32%) is added to the mixture at 0 to +5° C. within 30 to 45 minutes and the dropping funnel is rinsed with water (10 ml). After confirming that the conversion has proceeded to a satisfactory level by HPLC, the mixture is worked up by extracting repeatedly with t-butyl methyl ether (3×50 ml). The collected organic phases are washed twice with 10% aqueous bisulfite (50 ml) and once with water (40 ml). Finally, the product solution is dried and the solvent is evaporated in vacuum to yield the crude product as a yellow oil, which crystallized on standing (mp 80-81° C.). If the already pure product needs further purification, it can be crystallized from ether/hexane (m.p82-83° C.).

$^1$H-NMR (CDCl$_3$) δ(ppm): 3.05 (d, 1H), 3.92 (s, 3H), 5.45 (d, 1H), 5.82 (s, 1H), 6.91-6.96 (m, 1H); 6.98-7.04 (m,2H)

E5.2 4-(2-Amino-ethyl)-2-methoxy-phenol

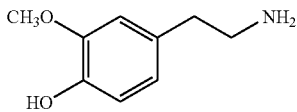

A solution of hydroxy-(4-hydroxy-3-methoxy-phenyl)-acetonitrile (9.0 g) in ethanol (50 ml) is added to a mixture of 10% palladium on charcoal (0.8 g), anhydrous ethanol (100 ml) and concentrated sulfuric acid (6.7 g) over a period of 2 hours at room temperature, while hydrogen is introduced simultaneously into the reaction mixture. Hydrogen addition is continued for 1 hour at room temperature. After the catalyst is removed by hot-filtration at +70° C., most of the ethanol is removed (approx. 70%) by distillation. The remainder is cooled to a temperature of 0° C., at which the hydrogen sulfate of the desired aminophenol crystallizes on standing. The obtained white crystals are dissolved in 50 ml of water and the pH of the solution is adjusted to 10.5. The product precipitates during the neutralization as off-white crystals. Finally, 4-(2-amino-ethyl)-2-methoxy-phenol is collected by filtration (m.p. 156-158° C.).

$^1$H-NMR (d$_6$-DMSO) d(ppm): 2.3-2.4 (m, 2H together with DMSO); 2.5 (t, 2H); 2.5-3.6 (broad, 3H together with H$_2$O); 3.5 (s, 3H); 6.2-6.6 (m, 3H).

E5.3: 4-(2-Amino-ethyl)-2-methoxy-phenol

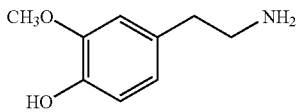

A solution of sodium cyanide (10.2 g) in water (50 ml) is added to a mixture of vanillin (15.5 g) and methanol (30 ml) at 0° C. Concentrated hydrochloric acid (28.5 g 32%) is introduced at 0° C. to +5° C. within 30 to 45 minutes. After confirming that the conversion has proceeded to a satisfactory level by HPLC, the mixture is extracted with t-butyl methyl ether (100 ml). After aqueous layer is drained, the organic phase is washed twice with 10% aqueous bisulfite (50 ml) and once with water (40 ml). The obtained crude cyanohydrin-solution is dried over sodium sulfate right after work-up. Most of the solvent is removed in vacuum and the remainder is dissolved in anhydrous, acidified methanol (50 ml). The methanolic solution is added to a mixture of 10% palladium on charcoal (1.4 g), anhydrous methanol (100 ml) and concentrated sulfuric acid (13.0 g) over a period of 1 hour at room temperature, while the mixture is kept under a pressurized hydrogen atmosphere. Hydrogen addition is continued for 3 hour at room temperature. After water (80 ml) is added, the catalyst is removed by filtration, and most of the methanol is removed by distillation. During the adjustment of the pH of the obtained solution to 10.5, the aminophenol precipitates as a sticky semisolid, which slowly crystallized on further stirring at room temperature. The crystallized product is isolated by filtration. The retained light yellow crystals are dried in vacuum (m.p. 156-158° C.).

$^1$H-NMR (d$_6$-DMSO) d(ppm):2.3-2.4 (m, 2H/DMSO); 2.5 (t, 2H); 2.5-3.6 (broad, 3H/H$_2$O); 3.5 (s, 3H); 6.2-6.6 (m, 3H).

E6: 2-(4-Chloro-phenyl)-N-[2-(3-methoxy-4-prop-2-ynyloxy-phenyl)-ethyl]-2-prop-2-ynyloxy-acetamide

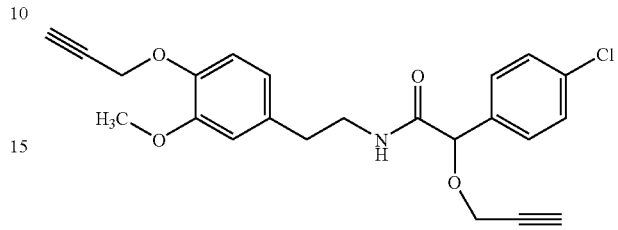

Method A:

A 80% solution of propargyl bromide in toluene (39,1 g, 0,263 mol) is added slowly at room temperature to a mixture of 2-(4-chloro-phenyl)-2-hydroxy-N-[2-(4-hydroxy-3-methoxy-phenyl)-ethyl]-acetamide (35.25 g, 0,105 mol), 30% sodium hydroxide solution (52,4 ml, 0,524 mmol) and tetrabutylammonium bromide (1,8 g) in 180 ml of dichloroethane. The reaction mixture is stirred for 16 hours at +40° C. Subsequently the mixture is evaporated and the residue is diluted with water (100 ml) and dichloroethane (100 ml). The organic phase is separated and the aqueous layer is extracted with dichloroethane. The combined organic phases are washed with brine (150 ml), dried over sodium sulfate and evaporated. The remaining oil is purified by chromatography on silica gel (ethyl acetate/hexane 1:1) to yield 2-(4-chloro-phenyl)-N-[2-(3-methoxy-4-prop-2-ynyloxy-phenyl)-ethyl]-2-prop-2-ynyloxy-acetamide, m.p. 90-92° C.

$^1$H-NMR (300 MHz, CDCl$_3$): 2.42(t, 1H), 2.47(t, 1H), 2.74 (t, 2H), 3.50(t, 2H), 3.79(s, 3H), 3.91(dd, 1H, 4.14(dd, 1H), 4.69(d, 2H), 4.91(s, 1H), 6.62-7.29(m, 7H).

Method B:

A mixture of 2-(4-chloro-phenyl)-2-hydroxy-N-[2-(4-hydroxy-3-methoxy-phenyl)-ethyl]-acetamide (5.6 g), 30% potassium hydroxide solution (5.6 g), methyl-tributylammonium chloride (0.43 g) and water (9.7 g) is stirred at room temperature. Methanesulfonic acid prop-2-ynyl ester (10 g) is added dropwise over a period of 2 hours. and stirring is continued at room temperature for further 4 hours. The mixture is allowed to separate and the aqueous phase is discarded. To the remaining organic phase a 30% potassium hydroxide solution (2.8 g), methyl-tributylammonium chloride (0.3 g) and water (2.8 g) are added and the reaction mixture is stirred at room temperature. During 1 hour the methanesulfonic acid prop-2-ynyl ester (5 g) is added. Stirring is continued for 18 hours at room temperature for 18 hours before the triethylamine (1.1 g) is added and the mixture is stirred at room temperature for another 30 minutes. Toluene (10 g) is added and the mixture is allowed to s separate. After discarding the aqueous phase the organic phase is washed with 15% hydrochloric acid. Then 10 g of acetone are added to the organic phase and it is washed with a 8.7% sodium hydrogen carbonate solution (3 g). The organic phase is collected and the solvent is evaporated, yielding the desired 2-(4-chloro-phenyl)-N-[2-(3-methoxy-4-prop-2-ynyloxy-phenyl)-ethyl]-2-prop-2-ynyloxy-acetamide, which exhibits identical physico-chemical data as the product prepared by Method A is obtained.

The invention claimed is:

1. A process for the preparation of 2-phenyl-2-hydroxy-N-[2-(3-alkoxy-4-hydroxyphenyl)-ethyl]-acetamides of the formula I

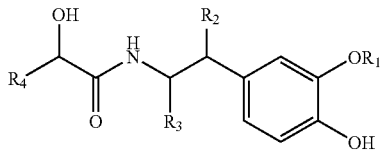

wherein $R_1$ is alkyl, $R_2$, and $R_3$ are each independently hydrogen or alkyl, and $R_4$, is optionally substituted aryl or optionally substituted heteroaryl, which process comprises reacting a nitrostyrene of the formula IV

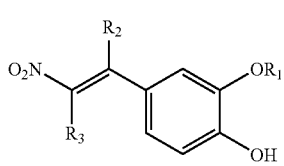

wherein $R_1$, $R_2$ and $R_3$ are as defined above, with reducing agent to form a 2-phenyl-nitroethane derivative of the formula V,

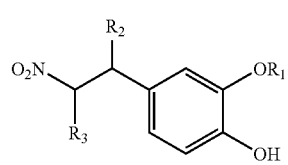

wherein $R_1$ $R_2$ and $R_3$ are as defined above; and further reacting this intermediate 2-phenyl-nitroethane derivative of the formula V with hydrogen in the presence of a catalyst to obtain a 2-(3-alkoxy-4-hydroxyphenyl)-ethylamine of the formula II

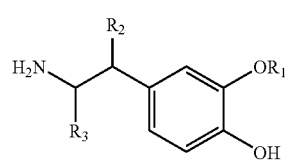

wherein $R_1$ $R_2$ and $R_3$ are as defined above, and reacting it with a α-hydoxycarboxylic acid ester of the formula III or a dioxolanone of the formula IIIa

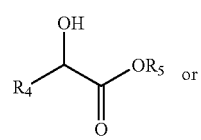

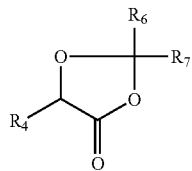

wherein $R_4$ is as defined above, and $R_5$, $R_6$ and $R_7$ independently of each other are lower alkyl.

2. A process according to claim 1, wherein $R_1$ is $C_1$-$C_8$alkyl; and $R_2$ and $R_3$ are independently of each other hydrogen or $C_1$-$C_4$alkyl; and $R_4$ is aryl or heteroaryl, each optionally substituted with substituents selected from to group comprising alkyl, alkenyl, alkynyl, cycloalkyl, cycloalkylalkyl, phenyl and phenylalkyl, where all these groups may be substituted with one or more substituents selected from the group comprising halogen; alkoxy, alkenyloxy, alkynyloxy; alkoxyalkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl.

3. A process according to claim 1, wherein $R_2$ and $R_3$ is hydrogen, methyl or ethyl, preferably methyl; and $R_4$ is phenyl, naphthyl or biphenyl, each optionally substituted by one to three substituents selected from the group comprising $C_1$-$C_8$alkyl, $C_2$$C_8$alkenyl, $C_2$-$C_8$alkynyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfonyl, halogen, cyano, nitro and $C_1$-$C_8$alkoxycarbonyl.

4. A process according to claim 1, wherein the reaction of a 2-(3-alkoxy-4-hydroxyphenyl)-ethylamine of the formula II with a α-hydoxycarboxylic acid ester of the formula III or a dioxolanone of the formula IIIa is carried out in the absence of a solvent at or above the melting point of the reaction mixture.

5. A process acccording to claim 1, wherein the α-hydroxycarboxylic acid ester of the formula III or the dioxolanone of the formula IIIa and the 2-(3-alkoxy-4-hydroxyphenyl)-ethylamine of the formula II is used in a molar ratio within the range of from 1:2 to 1:1.

6. A process according to claim 1, wherein a 2-(3-alkoxy-4-hydroxyphenyl)-ethylamine of the formula II is reacted with a α-hydoxycarboxylic acid ester of the formula III.

7. A process according to claim 1, wherein 2-(3-alkoxy-4-hydroxyphenyl)-ethylamine of the formula II is reacted with a dioxolanone of the formula IIIa.

8. A process for the preparation of 2-phenyl-2-hydroxy-N-[2-(3-alkoxy-4-hydroxyphenyl)-ethyl]-acetamides of the formula I

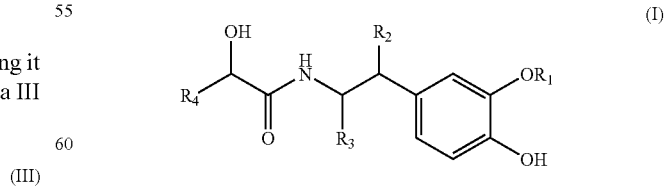

wherein $R_1$ is alkyl, $R_2$, and $R_3$ are each independently hydrogen or alkyl, and $R_4$, is optionally substituted aryl or optionally substituted heteroaryl, which process comprises reacting a carbonyl compound of the formula VIII

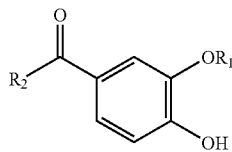
(VIII)

wherein $R_1$ and $R_2$ are as defined above, with hydrogen cyanide to form an α-hydroxynitrile of the formula IX

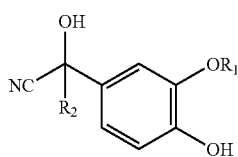
(IX)

wherein $R_1$ and $R_2$ are as defined above, and further reacting the α-hydroxynitrile of the formula IX with hydrogen in the presence of a catalyst to form a 2-(3-alkoxy-4-hydroxyphenyl)-ethylamine of the formula II

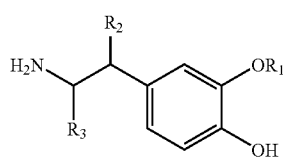
(II)

wherein $R_1$ $R_2$ and $R_3$ are as defined above and reacting it with a α-hydoxycarboxylic acid ester of the formula III or a dioxolanone of the formula IIIa

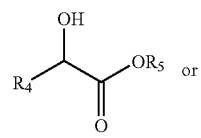
(III)

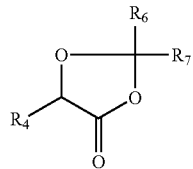
(IIIa)

wherein $R_4$ is as defined above, and $R_5$, $R_6$ and $R_7$ independently of each other are lower alkyl.

9. A process according to claim 8, wherein $R_1$ is $C_1$-$C_8$alkyl; and $R_2$ and $R_3$ are independently of each other hydrogen or $C_1$-$C_4$alkyl; and $R_4$ is aryl or heteroaryl, each optionally substituted with substituents selected from to group comprising alkyl, alkenyl, alkynyl, cycloalkyl, cycloalkylalkyl, phenyl and phenylalkyl, where all these groups may be substituted with one or more substituents selected from the group comprising halogen; alkoxy, alkenyloxy, alkynyloxy; alkoxyalkyl; haloalkoxy; alkylthio; haloalkylthio; alkylsulfonyl; formyl; alkanoyl; hydroxy; cyano; nitro; amino; alkylamino; dialkylamino; carboxyl; alkoxycarbonyl; alkenyloxycarbonyl and alkynyloxycarbonyl.

10. A process according to claim 8, wherein $R_2$ and $R_3$ is hydrogen, methyl or ethyl, preferably methyl; and $R_4$ is phenyl, naphthyl or biphenyl, each optionally substituted by one to three substituents selected from the group comprising $C_1$-$C_8$alkyl, $C_2$-$C_8$alkenyl, $C_2$-$C_8$alkynyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfonyl, halogen, cyano, nitro and $C_1$-$C_8$alkoxycarbonyl.

11. A process according to claim 8, wherein the reaction of a 2-(3-alkoxy-4-hydroxyphenyl)-ethylamine of the formula II with a α-hydoxycarboxylic acid ester of the formula III or a dioxolanone of the formula IIIa is carried out in the absence of a solvent at or above the melting point of the reaction mixture.

12. A process according to claim 8, wherein the α-hydroxycarboxylic acid ester of the formula III or the dioxolanone of the formula IIIa and the 2-(3-alkoxy-4-hydroxyphenyl)-ethylamine of the formula II is used in a molar ratio within the range of from 1:2 to 1:1.

13. A process according to claim 8, wherein a 2-(3-alkoxy-4-hydroxyphenyl)-ethylamine of the formula II is reacted with a α-hydoxycarboxylic acid ester of the formula III.

14. A process according to claim 8, wherein a 2-(3-alkoxy-4-hydroxyphenyl)-ethylamine of the formula II is reacted with a dioxolanone of the formula IIIa.

15. A process according to claim 8, wherein the α-hydroxynitrile of the formula IX is is introduced portionwise into the hydrogenation reactor in order to minimise the formation of free hydrogen cyanide in the reaction mixture.

* * * * *